(12) United States Patent
Fleshman

(10) Patent No.: US 7,981,053 B2
(45) Date of Patent: Jul. 19, 2011

(54) SPECIMEN COLLECTION DEVICE

(76) Inventor: Barbara Fleshman, Potomac Falls, VA (US)

(*) Notice: Subject to any disclaimer, the term of this patent is extended or adjusted under 35 U.S.C. 154(b) by 0 days.

(21) Appl. No.: 12/646,910

(22) Filed: Dec. 23, 2009

(65) Prior Publication Data
US 2010/0174209 A1   Jul. 8, 2010

Related U.S. Application Data

(60) Provisional application No. 61/142,622, filed on Jan. 5, 2009.

(51) Int. Cl.
*A61B 5/20* (2006.01)
(52) U.S. Cl. .................................. 600/574; 600/573
(58) Field of Classification Search .................. 600/573, 600/574
See application file for complete search history.

(56) References Cited

U.S. PATENT DOCUMENTS

| | | | | |
|---|---|---|---|---|
| 6,719,951 | B1* | 4/2004 | Griffith | 422/102 |
| 7,128,352 | B1* | 10/2006 | Phippen | 294/1.5 |
| 2005/0241964 | A1* | 11/2005 | Taylor | 206/170 |
| 2008/0154219 | A1* | 6/2008 | Longo et al. | 604/327 |
| 2008/0228106 | A1* | 9/2008 | Forte et al. | 600/575 |
| 2009/0076413 | A1* | 3/2009 | Robles | 600/573 |

* cited by examiner

*Primary Examiner* — Max Hindenburg
*Assistant Examiner* — Michael C Stout

(57) ABSTRACT

The present disclosure provides a novel, disposable urine collection vessel securing device that can be used in combination with any standard urine containment vessel and configured to provide an inexpensive, sanitary, convenient device for the collection of urine from a subject. Also provided is a method of use and can be included as one of the items in a sample collection kit.

14 Claims, 7 Drawing Sheets

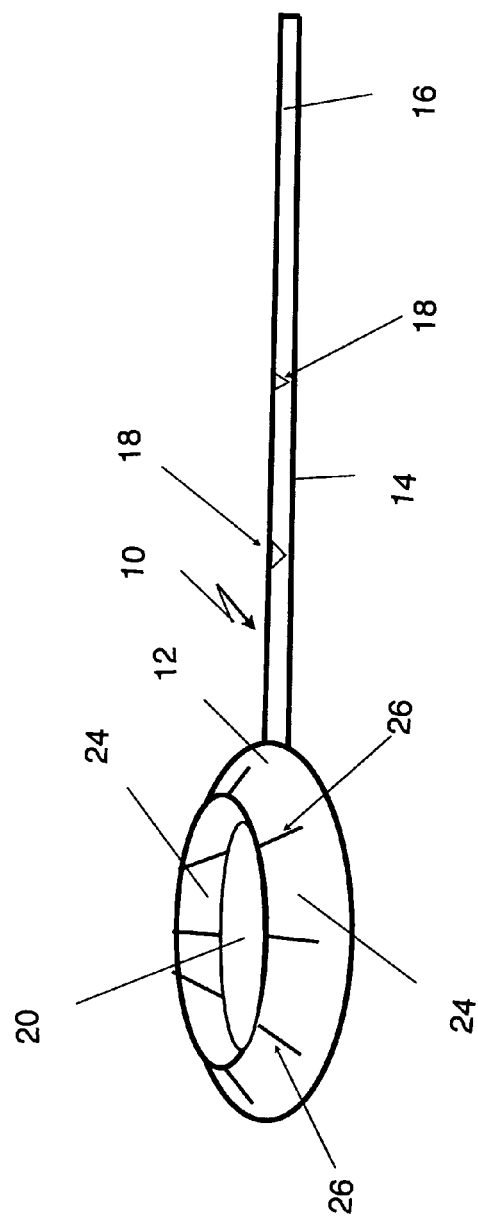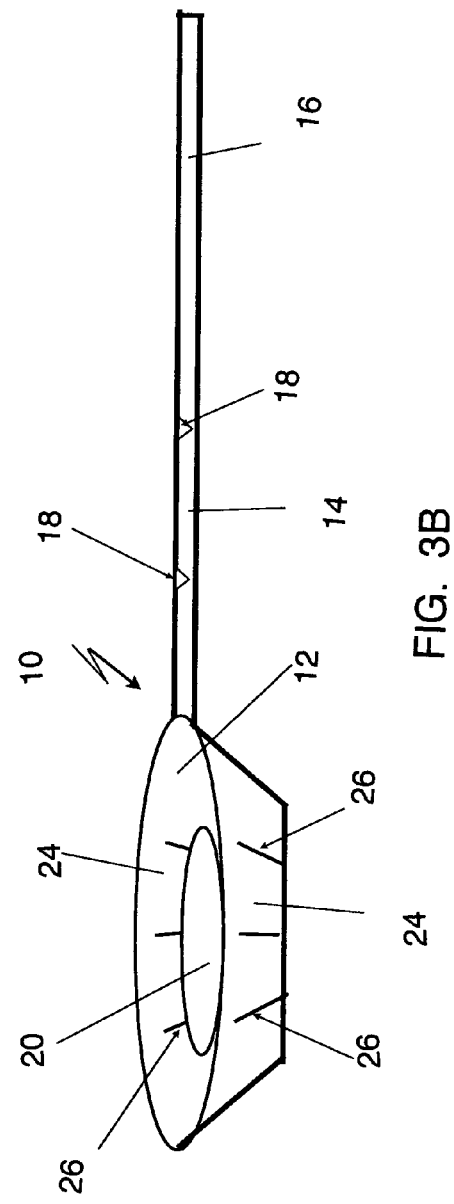
FIG. 3A
FIG. 3B

SPECIMEN COLLECTION DEVICE

CROSS REFERENCE TO RELATED APPLICATIONS

This application claims the benefit of:
U.S. Provisional Application 61/142,622, entitled "Specimen Collection Device" filed Jan. 5, 2009.

BACKGROUND OF THE INVENTION

1. Technical Field

The present invention relates to devices for facilitating the collection of bodily fluid specimens from subjects. Particularly the present invention is directed to a novel fluid specimen collection device that can be used in combination with a specimen containment vessel to provide a convenient, inexpensive specimen collection system that facilitates sanitary collection of fluid specimens. More particularly the present invention is directed to a novel disposable urine collection device that can be used in combination with any standard urine containment vessel and configured to provide an inexpensive, sanitary, convenient device for the collection of urine from a subject.

2. Background Art

A routine medical diagnostic procedure is to conduct analysis on urine samples collected from patients. Typically when collecting urine samples for medical testing and analysis, patients are provided a urine specimen collection container and often are instructed to catch a mid-stream sample of urine so as to provide a sample with minimal contamination. Female patients are also frequently provided with a packaged sterile wipe and instructed to cleanse the vaginal area prior to attempting to catch a mid-stream urine sample omen are provided a specimen collection container for use after cleansing the vaginal area of topical bacteria. They then must either sit or squat over the toilet and hold the collection container in their hand while voiding a small amount of urine into the toilet before collecting a midstream specimen. This must be done while attempting to strategically position the container below the urine stream. This technique can be very challenging for all women, but especially pregnant, overweight, or elderly females. The current process most often results in urine splashing on the sides of the container and on the patient's hands as they attempt to collect the urine. This creates an unsanitary as well as repugnant situation for the patient and the nurse/technician who subsequently must handle the contaminated containers. The situation is no less repugnant for the severely obese patient, male or female or for the young child in need of adult assistance.

Previous efforts to provide devices to assist in the sterile collection process of urine specimens have been large unwieldy and expensive devises designed more for the physician's/technician's ease of use to collect uncontaminated and sterile urine specimens. Other efforts have attempted to provide devices that are made from non-biodegradable material that are expensive to produce and therefore cost prohibitive as a one-time-use, disposable product. Examples of such conventional devices are described in U.S. Pat. No. 7,000,963 issued to Dodd et al., U.S. Pat. No. 6,299,606 issued to Young, U.S. Pat. No. 3,583,388 (Hovick), U.S. Pat. No. 3,635,091 issued to Linzer et al., U.S. Pat. No. 3,722,503 issued to Hovick, U.S. Pat. No. 3,750,647 issued to Gleason et al.), U.S. Pat. No. 3,830,107 issued to Linzer et al., U.S. Pat. No. 3,943,770 issued to McDonald, U.S. Pat. No. 3,982,898 issued to McDonald, U.S. Pat. No. 4,040,791 issued to Kuntz, U.S. Pat. No. 4,094,020 issued to Franklin, U.S. Pat. No. 4,276,889 issued to Kuntz et al., and U.S. Pat. No. 4,331,162 issued to Kuntz et al. Such conventional efforts to provide a device to facilitate the collection of urine samples have consistently proven to be large, bulky or expensive to produce and further are not designed as biogradeable disposable devices for routine medical office collection.

As such, a need therefore remains for a disposable, inexpensively produced, simply operated device capable of facilitating easy, sterile, collection of urine specimens in a home, clinical, or hospital environment.

SUMMARY OF THE DISCLOSURE

The present invention meets the above identified need by providing a novel inexpensively produced, disposable, biodegradable device capable of use with a variety of conventional collection vessel types in the process of collecting a urine specimen.

Also provided is a novel device for use with a collection vessel, the device being easily configured at the time of use to adapt to different body shapes and sizes of patients from whom the urine specimen is to be collected.

Also provided is a novel selectively configured device constructed of biodegradable materials that can be used with a variety of collection vessels to facilitate the sanitary collection of a urine specimen from a subject.

Also provided is a novel device that can be used with a urine specimen collection vessel, the device including a grasping end and a collection vessel securing end that are connected by a connecting arm component.

Also provided is a novel device that can be used with a urine specimen collection vessel having a vessel securing end and a grasping end connected one to the other by a connecting arm, the arm being capable of being selectively configured as needed by the user.

Also provided is a novel device that can be used with a urine specimen collection vessel having a vessel securing end connected by a connecting arm to a grasping end, the connecting arm having at least one portion of the arm manufactured or treated to be predisposed to be selectively bent as needed by the user.

Also provided is a novel device for use with a urine collection specimen collection vessel, the device having a collection vessel securing end that defines there through a vessel receptacle, the receptacle having at least one inwardly directed flange and being flexible so as to bend to permit insertion of the collection vessel into the vessel receptacle and being resilient so as to exert an inward bias against the side of the vessel as to be capable of releasably securing the vessel within the vessel receptacle.

Also provided is a novel device for use with a urine collection specimen collection vessel, the device having a collection vessel securing end and a grasping end connected one to the other by a connecting arm, the grasping end being ergonomically configured to facilitate grasping and manipulation of the device by a user.

Also provided is a method of collecting a urine specimen, the method including providing a novel biodegradable device having a collection vessel securing end, a grasping end, and a connection arm connecting the one to the other, the connecting arm being capable of being selectively configured as needed by the user, the collection vessel securing end being ergonomically configured and capable of releasably securing a urine collection vessel; providing a urine collection vessel; releasably connecting the vessel to the collection vessel securing end; collecting a urine sample; and releasing the collection vessel from the device.

Also provided is a kit containing at least one novel device according to the present invention and at least one other component for use in collecting a urine specimen, such as, for example at least one collection vessel or at least one sterile wipe, the kit being provided within a package.

BRIEF DESCRIPTION THE DRAWINGS

The foregoing and other features of the disclosed device will become apparent to one skilled in the art to which the present invention relates upon consideration of the following description of exemplary embodiments with reference to the below listed accompanying drawings.

FIGS. 3A and 3B show a top perspective view of alternative embodiments of the present invention in having a collection vessel securing end in a non-planar configuration. FIG. 3a shows an alternative collection vessel securing end with a truncated conical configuration and FIG. 3B shows an alternative collection vessel securing end with a funnel-shaped configuration.

DETAILED DESCRIPTION OF PREFERRED EMBODIMENTS

Figure 1:
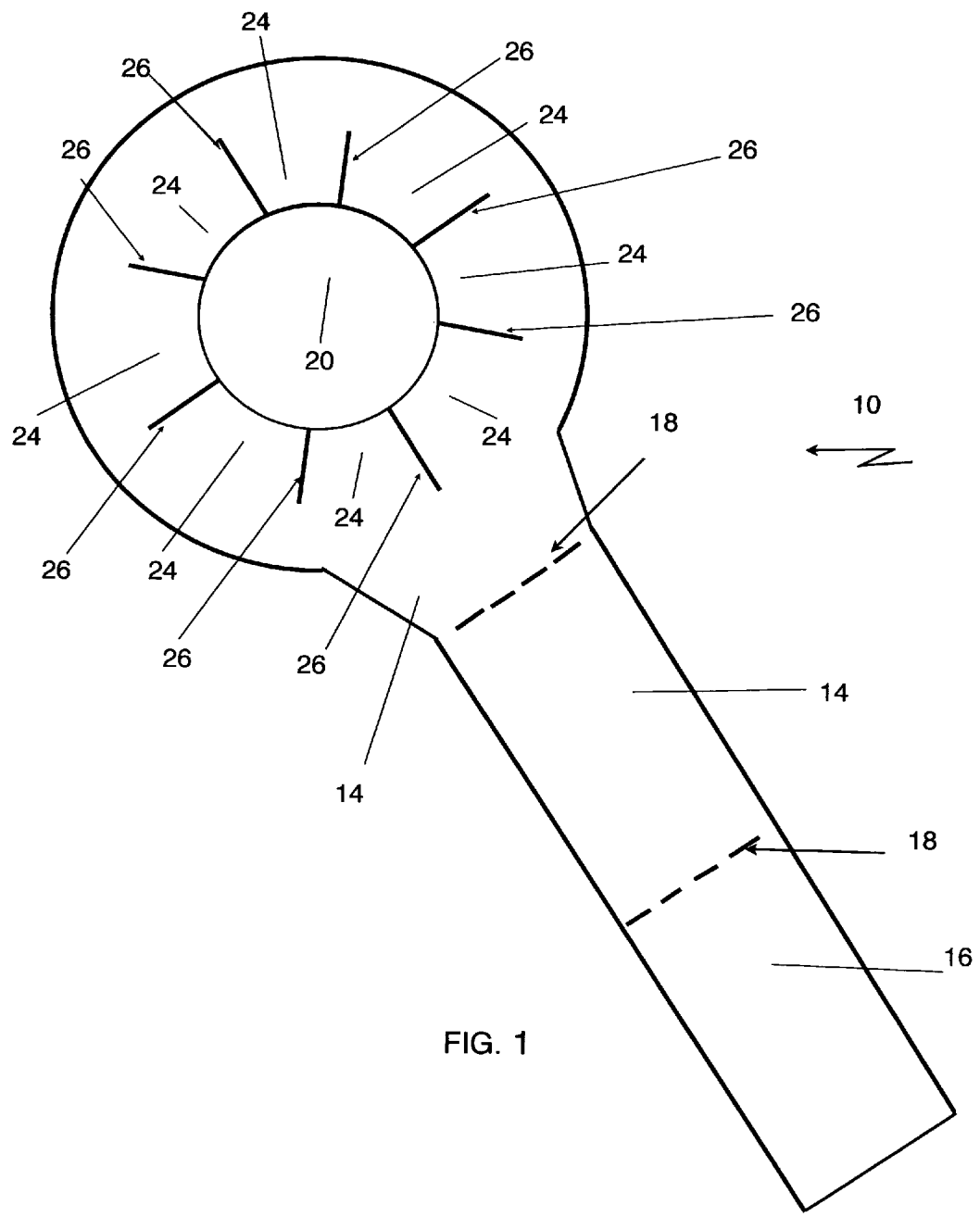
FIG. 1 shows a top view of the novel device of the present invention.

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The novel device of the present invention, generally shown at 10, in FIGS. 1-7 includes a collection vessel securing end 12 connected by a connecting arm 14 to a grasping end 16. The connecting arm 14 can be manufactured or treated to have at least one bending portion 18 provided to permit selective bending of the connecting arm 14 away from the flat plane of the connecting arm 14, as deemed necessary by a user. The bending portion 18, can be provided as one or more deformations in the structure of the connecting arm 14, as one or more perforated lines in the material of the connecting arm 14, as crimped transverse lineal portions at selected sites along the length of the connecting arm 14, or as any other structural manufacture or treatment of the material of the connecting arm 14 that is suitable to facilitate selective bending of the connecting arm 14.

The material used in the manufacture of the device 10 can be such as to have a combination of flexibility and strength to permit bending of the connecting arm 14 to a selected configuration while still being capable of holding that same selected configuration during use of the device 10. Non-limiting examples of suitable materials for manufacture of the device 10 include paper, cardboard, pressed paper laminate, plasticized coating material on any of the preceding materials, or any other material or combination of materials having combined characteristics of flexibility and resiliency to provide the bending and shape memory retention required of the invention when used. A non-limiting commercial example of a suitable alpha-cellulose material that is considered suitable or manufacture for the device 10 is Alphamat™ manufactured by Artcare Systems of Nielsen & Bainbridge headquartered at 40 Eisenhower Drive, Paramus, N.J. 07653.

Figure 4:
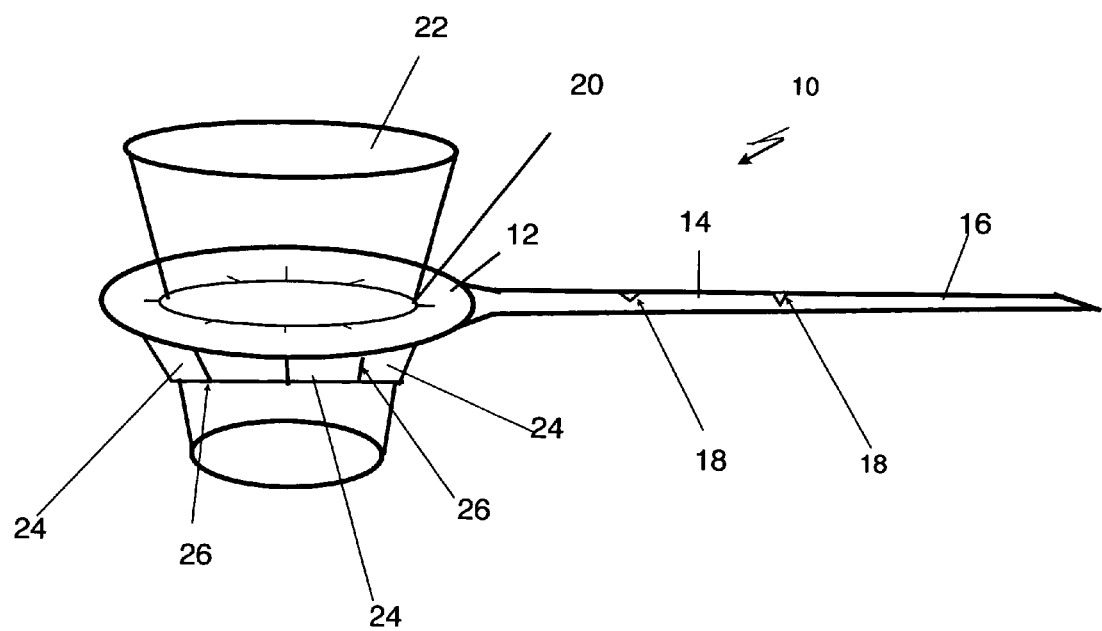
FIG. 4 shows a side perspective view showing the relationship of the device and the urine specimen collection container that is placed into the collection vessel securing end of the device of the present invention.

The collection vessel securing end 12 defines there through a vessel receptacle portal 20 that is sized and configured to receive any conventional urine collection vessel, such as that exemplified at 22 in FIG. 4. Historically, urine collection vessels were manufactured of plasticized paper or plastic with or without a securing cover. More recently urine collection containers are often manufactured of very thin plastic that tends to bend and crumple inwardly from the pressure of the hand/fingers of the holder when guiding the container into a position suitable to collect a urine sample from a patient.

Figure 5:
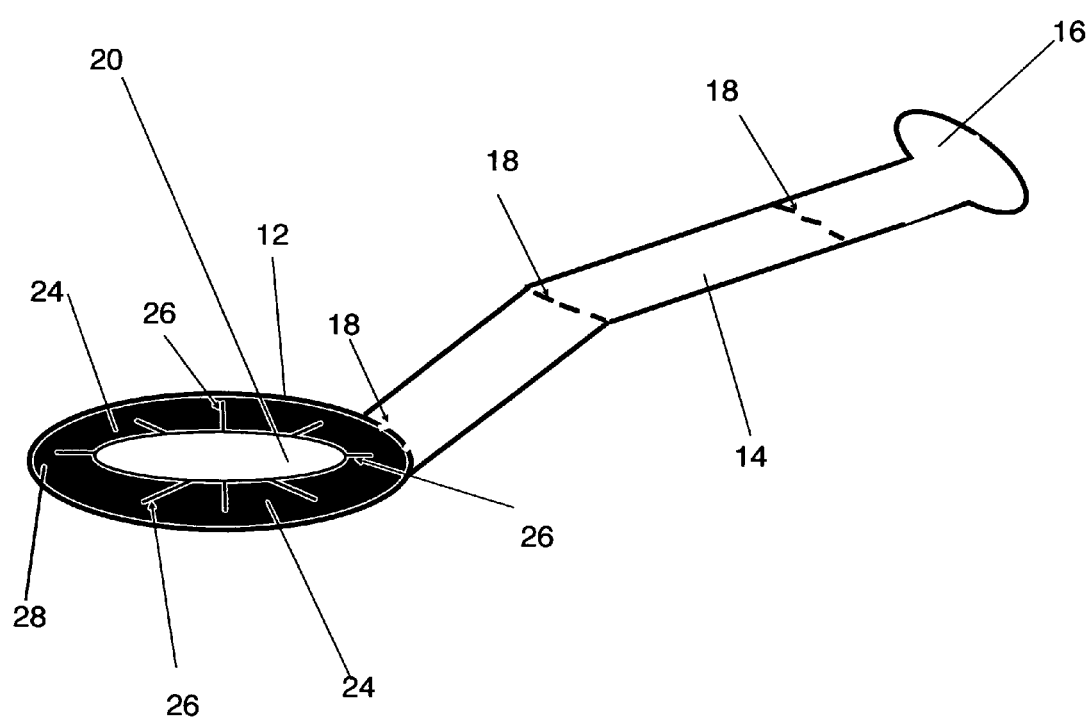
FIG. 5 shows a three quarter view of the novel device having a moisture absorbent surface on a portion of the device surface and also showing one of multiple ways in which the device can be bent along delineated points on the collection arm for more convenient grasp and handling during collection the novel device of the present invention.

As shown in FIG. 3A and FIG. 3B, the device 10 can alternatively be provided with a collection vessel securing end 12 that is configured to have a non-planar relationship to the basic planar shape of the device 10. That is, as in FIG. 3A, the collection vessel securing end 12 can be formed to have a conical shape so to as to deform the securing end 12 to have an upward truncated conical configuration as shown. Such an upward conical conformation of the collection vessel securing end 12 can beneficially allow for urine that errantly is not directed into the collection vessel 22, shown in FIG. 4, to be drained away and off the edge of the device 10, thus avoiding unwanted spillage from the surface of the device 10. As shown in FIG. 3B, this same principle can be applied in the reverse for such an alternative embodiment, in that instead of configuring the collection vessel securing end 12 upward into a truncated conical shape, it can be manufactured to have a downward funnel configuration. The alternative embodiment having a downward funnel-like configuration for the securing end 12 would allow urine errantly spilled on the surface of the device 10 to drain downward toward the outside of the collection vessel, shown at 22 in FIG. 4. The distortion of the flanges 24 caused by the presence of the collection vessel 22 would sufficiently open the space created by the flange cuts 26 to allow the spilled urine to pass through the cuts and away from the device 10. As shown in FIG. 5, a further alternative embodiment of the device 10 can include a moisture absorbent surface 28 over at least a portion of the device 10. Such an absorbent surface 28 could also assist in the prevention of unwanted spillage of urine from the device 10 after the urine specimen has been collected in the collection vessel 22, shown in FIG. 4. It is within the concept of the invention that the moisture absorbent surface 28 can be provided as a natural characteristic of the material selected for manufacture of the device 10 or it can be an applied surface coating.

Figure 2:
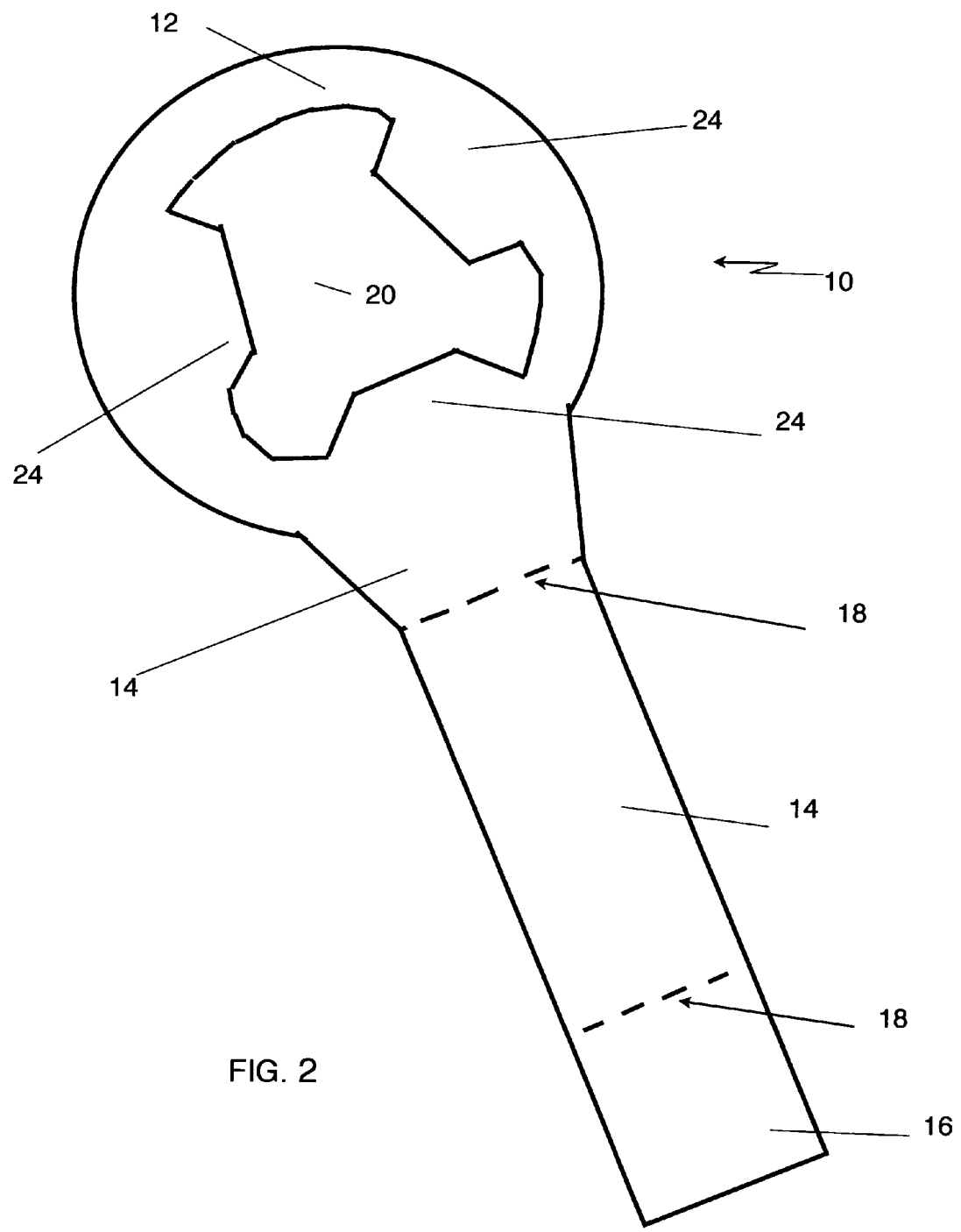
FIG. 2 shows a top view of the novel device of the present invention, wherein the collection vessel securing end of the device includes multiple, asymmetrical disposed, inwardly-directed flanges.

The device 10 is shown in FIG. 4 in combination with a urine collection vessel 22. The collection vessel 22 is releasably secured in the vessel receptacle portal 20 by an inwardly directed bias of at least one flange 24 extending into the space of the portal 20. Embodiments of the device 10 with multiple directly adjacent flanges 24 can include flange cuts 26, which permit restricted movement of the adjacent flanges 24 away from each other when a collection vessel 22 is forced into position in the vessel receptacle portal 20. The flexible yet resilient characteristics of the flanges 24 create sufficient pressure on the wall of the collection vessel 22 to securely hold the vessel 22 in place in the device 10. As shown, the insertion of the vessel 22 into the portal 20 can cause a distortion of the inwardly directed flanges 24. This distortion of the flanges 24 and the resilient tendency of the material of the flanges 24 to return to a planar inwardly directed disposition creates the gentle bias needed to releasably secure the vessel 22 in place during use of the device 10. Upon completion of the urine collection, the vessel 22 can be easily removed from the device 10 by simply lifting the vessel 22 upward out of the portal 20 and allowing the flanges 24 to return to their former planar disposition. While a preferred embodiment of the present invention provides a device 10 having a full compliment of adjacent inwardly directed flanges 24 as shown in FIGs. 1 and 3-7, it is within the concept of the invention to provide one, two, three, or more flanges 24, which may or may not be symmetrically disposed around the vessel receptacle portal 20. An example of such an alternative embodiment is shown in FIG. 2.

As shown in FIG. 5 the device 10 is configured with the connecting arm 14 bent at two distinct bending portions 18a and 18b along the length of the arm 14. A third bending portion 18c is left unbent. As shown, the device 10 can be reconfigured as desired by the user by bending or not bending the device 10 at any of the bending portions 18 so as to best meet the needs of a particular user. FIG. 5 also shows the device 10 having a wider area at the grasping end 16 of the stem. Such a variation in the width of the grasping end 16 or any other ergonomically directed configuration of the grasping end 16 can add stability and control when in the user's hand.

Figure 6:
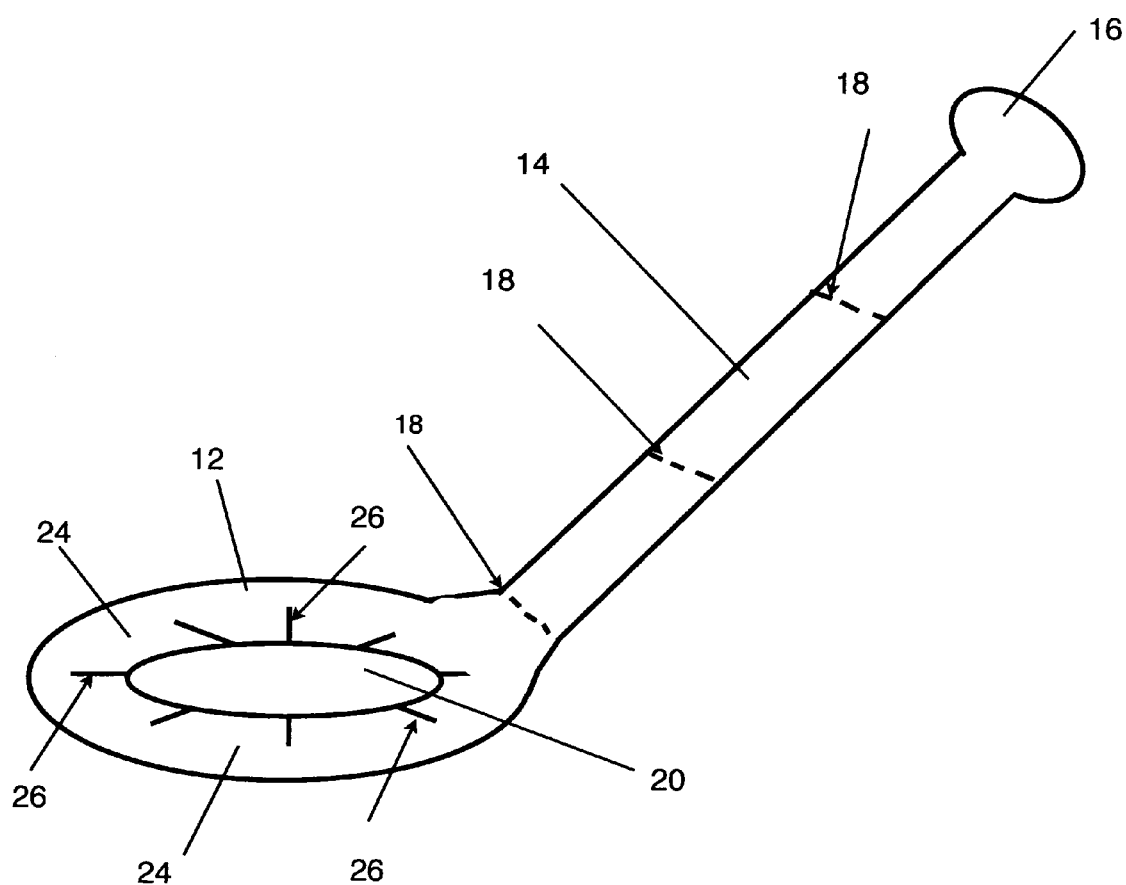
FIG. 6 shows is a three quarter view showing another option for bending the device for convenient handling/collection the novel device of the present invention.

As shown in FIG. 6 the device 10 can be selectively configured with the connecting arm 14 bent in only one place so as to permit the user to hold the grasping end 16 and direct the device 10 downward to obtain the collection of a urine specimen while the singular bend at the bending portion 18 serves to level the collection vessel securing end and the collection vessel 22 that would be securely held therein. For users of standard or physiologically normal size and stature, the configuration shown in FIG. 6 might be an optional configuration and thus preferred by the majority of users. However, not all users are of standard or normal physical size and stature and for that reason, the provision of multiple bending portions 18 to allow each user to customize the configuration of the device 10 is a need previously unfulfilled but herein provided by the present invention.

Figure 7:
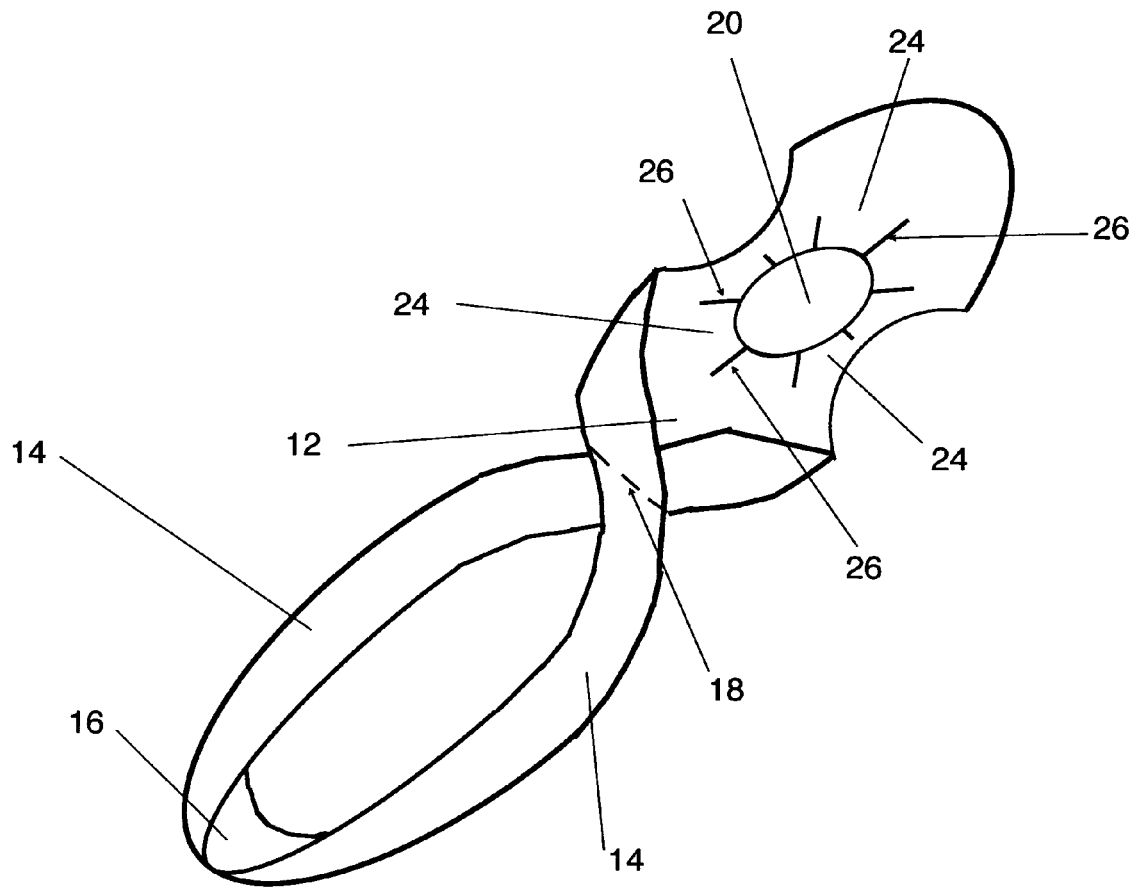
FIG. 7 shows a top view of a device according to the present invention having an ergonomically configured grasping end and an ergonomically configured collection vessel securing end.

As shown by the alternative embodiment depicted in FIG. 7, the device 10 can have an ergonomically configured collection vessel securing end 12. While the vessel receptacle portal 20 remains in a standard size and configuration to be capable of releasably securing any convention urine collection vessel, such as that shown at 22, the outer configuration of the vessel securing end 12 can be ergonomically shaped to better conform to the natural shape of the genital area and the adjacent thighs of a user. Also shown in FIG. 7 is an alternative shape for the connecting arm 14, being bifurcated to form a ribbon like shape terminating at the grasping end 16 in an easy to grasp loop handle design. While the ergonomic configurations shown in FIG. 7 can provide a particularly useful alternative design, the configurations shown are only exemplary and non-limiting to the scope of the present invention.

The present invention also provides a method of collecting a urine specimen, the method including providing a the device 10 and a urine collection vessel 22, and the user bending the connecting arm 14 of the device 10 into a conformation most suitable to the ergonomic needs of the user, collecting the urine sample, removing the vessel 22 and discarding the device 10. Advantageously, the device 10 can be made of biodegradable materials thus permitting the inexpensive, one-time use device 10 to be used to collect a urine sample in a sanitary method, avoiding spillage and urine contact to the hands of the user and then to be disposed on in an environmentally friendly manner.

Also provided is a kit containing at least one novel device 10 according to the present invention and at least one other component for use in collecting a urine specimen, such as, for example at least one collection vessel 22 or at least one sterile wipe, the kit being provided within a package.

Each of the embodiments described above are provided for illustrative purposes only and it is within the concept of the present invention to include modifications and varying configurations without departing from the scope of the invention that is limited only by the claims included herewith.

What is claimed is:

1. A urine collection vessel securing device comprising:
a device body comprising a collection vessel securing end, a grasping end, and a connecting arm connecting said securing end to said grasping end, said securing end defining there through a collection vessel receptacle portal and said connecting arm comprising at least one pre-positioned bending portion,
wherein said collection vessel receptacle portal is configured to selectively secure and release a urine collection vessel and said at least one bending portion is capable of being manually bent to a selected configuration by the user,
wherein the collection vessel securing end is ergonomically configured being elongated from front to back in an oval configuration making the collection vessel securing end narrower side to side with a portion of each side recessed in formation to accommodate physical contours of a subject including pregnant, handicapped, or overweight persons when positioning the urine collection vessel held by collection vessel receptacle portal during collection of a urine specimen.

2. The device of claim 1, wherein said securing end comprises at least one flange inwardly directed from said securing end into said collection vessel receptacle portal.

3. The device of claim 2, wherein said at least one flange includes multiple flanges.

4. The device of claim 3, wherein said multiple flanges are symmetrically disposed around the circumference of said collection vessel receptacle portal.

5. The device of claim 2, wherein said flanges are capable of exerting an inward bias when said flanges are displaced by insertion of a collection vessel into said collection vessel receptacle portal.

6. The device of claim 5, wherein said multiple flanges are adjacently aligned around the circumference of said collection vessel, said adjacent flanges being separated by a complimentary number of multiple flange cuts extending radially away from said collection vessel receptacle portal.

7. The device of claim 1, wherein said at least one bending portion comprises a manufactured or treated pre-selected portion of said connecting arm.

8. The device of claim 7, wherein said pre-selected portion of said connecting arm is crimped, deformed, or perforated to facilitate bending at said portion.

9. The device of claim 1, wherein said grasping end is ergonomically configured to facilitate manual grasping of said device.

10. The device of claim 1, wherein said collection vessel securing end and said grasping end are ergonomically configured.

11. The device of claim 1, further comprising a moisture absorbent surface on at least a portion of said device.

12. The device of claim 1, wherein said device is manufactured biodegradable materials.

13. The device of claim 1, further containing a sterile wipe, wherein the device including the collection securing end, the grasping end, the grasping arm and the receptacle portal are included together in a kit.

14. A urine collection vessel securing device comprising: a device body comprising a collection vessel securing end, a grasping end, and a connecting arm connecting said securing end to said grasping end, said securing end defining there through a collection vessel receptacle portal and said connecting arm comprising at least one pre-positioned bending portion,
   wherein said collection vessel receptacle portal is configured to selectively secure and release a urine collection vessel and said at least one bending portion is capable of being manually bent to a selected configuration by the user,
   wherein the collection vessel securing end is ergonomically configured being elongated from front to back in an oval configuration making the collection vessel securing end narrower side to side with a portion of each side recessed in formation to accommodate physical contours of a subject including pregnant, handicapped, or overweight persons when positioning urine collection vessel held by collection vessel securing device during collection of a urine specimen,
   wherein the surface of the collection vessel Securing end includes a moisture absorbent coat to add to sanitary handling of a urine collection vessel when collecting a urine specimen.

* * * * *